United States Patent [19]

Holtkamp, Sr.

[11] Patent Number: Plant 6,587

[45] Date of Patent: Feb. 7, 1989

[54] AFRICAN VIOLET PLANT NAMED SONJA

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 55,878

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

An African violet plant named Sonja, characterized by its violet-shaped, but round-looking purple flowers with wavy edges; upright flower stems, producing a nice bouquet above the foliage; profuse flowering; vigorous growth habit; round to oval medium green leaves; long-lasting and non-dropping flowering habit.

1 Drawing Sheet

The present invention comprises a new and distinct cultivar of African violet plant, botanically known as *Saintpaulia ionantha,* and hereinafter referred to by the cultivar name Sonja.

The new cultivar was referred to during the breeding and selection process by the designation 139/9, and is a product of a planned breeding program. The new cultivar was originated from a cross made by applicant in a controlled breeding program in Haffen, Federal Republic of Germany. The female, or seed parent was a cultivar designated 68, named Arkansas, and disclosed in U.S. Plant Pat. No. 5,725. The male, or pollen parent was a cultivar designated E168 Lilac.

Sonja was discovered and selected by me as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Sonja has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Sonja which in combination distinguish this African violet as a new and distinct cultivar:

1. Violet-shaped, but round-looking purple flowers with wavy edges.
2. Forms a nice bouquet on strong upright flower stems.
3. Each plant has 8–9 stems each of which carries 8 to 9 and more single flowers.
4. Profuse flowering.
5. Seed capsule pushes slightly through.
6. Vigorous grower.
7. Plant saleable 10–11 weeks after potting.
8. Long-lasting, non-dropping flowers.

9. After maturity, the flowers dry off and remain on the peduncle without becoming infected by botrytis.
10. Round to oval, medium green leaves.

The accompanying color photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values were taken under natural light conditions at approximately 2:00 p.m. in Nashville, Tenn. Under cooler conditions and more intensive lighting the purple color becomes more intense.

Botanical classification: *Saintpaulia ionantha,* Ramat., cv. Sonja.

Parentage:

*Male parent.*—E168 Lilac.

*Female parent.*—68, named Arkansas.

Propagation: The new cultivar holds its distinguishing characteristics through successive propagations by leaf cuttings and by division of shoots.

Plant: From 9 to 11 cm tall when grown in pots, and approximately 22–26 cm in diameter when fully grown. The growth rate is vigorous.

*Leaves.*—Shape: Round to oval. Diameter: 60–80 mm. Texture: Velvety. Aspect: Slightly shiny, hairy. Ribs and veins: Upperside well visible, underside very well pronounced, light green and shiny. Color (upper side): Green 139A. Color (under side): Slightly reddish veins, green 138D in between. Petioles: Light green, hairy, occasionally with purplish touch.

*Flowers.*—Buds: Purple, ball-shaped, hairy, 8–9 mm before opening. Sepals: Five (5) in number, purplish-green. Calyx: Funnel-shaped. Aspect: Spear-shaped, hairy. Peduncle: Strong, upright, purplish.

*Individual flowers.*—Size: 40 to 45 mm in diameter. Shape: Violet-shaped petals with wavy edges. Color (upper side): Purple violet 80A-B. Color (under side): Purple violet 80B-C. Borne: Each flower stem carries 8–9 and more flowers on strong, upright peduncles that are free standing above the leaves. Flowering habit: Flowers 9–10 weeks after potting; flowering profuse.

*Reproductive organs.*—Stamens: Two (2) in number. Anthers: Two, composed of 4 anther cells, seed capsule pushes slightly through. Filaments: 4–5 mm long, yellowish green, with dark purple on edge. Pollen color: Yellow 7A. Styles: Purple, 7–8 mm, base of ovary light green.

*Roots.*—Establish well, white, turning slightly brownish when older.

Disease resistance: Good.

General observations: Sonja is a very attractive, vigorous grower with medium green, round to oval leaves. Approximately 9–10 weeks after potting the plant has developed 8–9 strong upright flower stems which carry 8–9 and more round looking flowers with wavy edges. The single purple flowers contrast nicely with the bright yellow anthers. The 2 smaller petals have a darker center. The flowers form a compact flower head that is free standing above the leaves. The flowers are long-lasting and non-dropping, and the seed capsule pushes slightly through.

I claim:

1. A new and distinct cultivar of African violet named Sonja, as described and illustrated, and particularly characterized by its violet-shaped, but round-looking purple flowers with wavy edges; upright flower stems, producing a nice bouquet above the foliage; profuse flowering; vigorous growth habit; round to oval medium green leaves; and long lasting and non-dropping flowering habit.

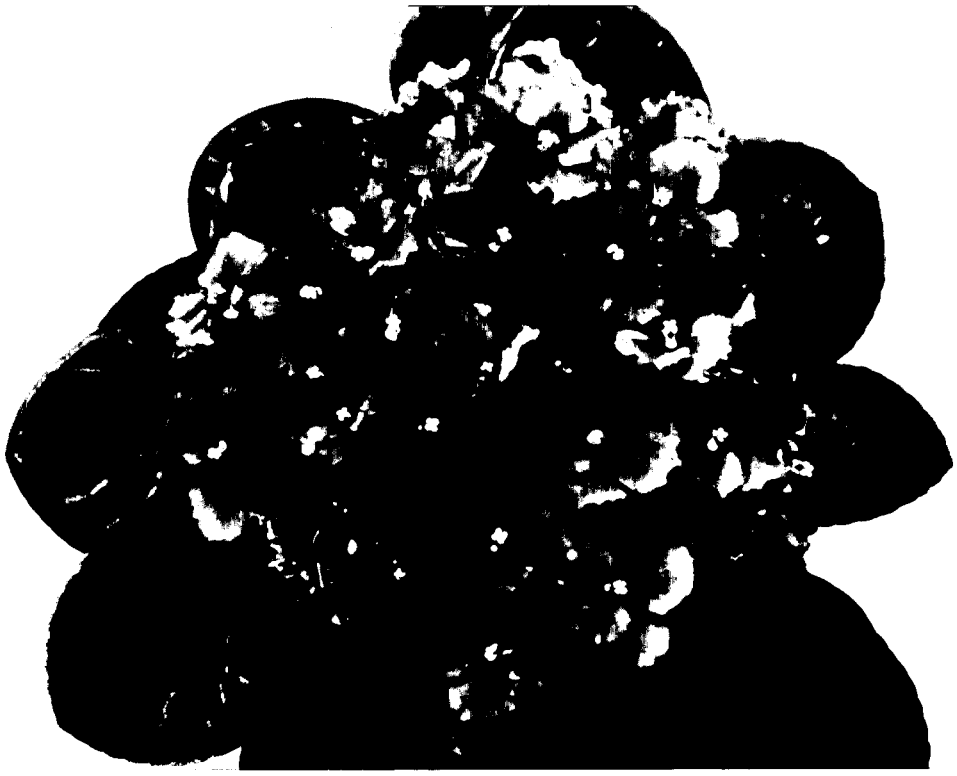

* * * * *